(12) United States Patent
Regni, Jr.

(10) Patent No.: US 6,343,931 B1
(45) Date of Patent: Feb. 5, 2002

(54) BONE AUGMENTATION METHOD AND APPARATUS

(76) Inventor: Gerald J. Regni, Jr., 937 Christian St., Phila, PA (US) 19147

( * ) Notice: Subject to any disclaimer, the term of this patent is extended or adjusted under 35 U.S.C. 154(b) by 0 days.

(21) Appl. No.: 09/392,383

(22) Filed: Sep. 9, 1999

(51) Int. Cl.[7] .............................. A61C 3/00; A61C 5/00
(52) U.S. Cl. ..................... 433/175; 433/201.1; 433/215
(58) Field of Search ................................. 433/172, 173, 433/174, 175, 176, 201.1, 215

(56) References Cited

U.S. PATENT DOCUMENTS

| | | | | |
|---|---|---|---|---|
| 4,411,624 A | * | 10/1983 | Ogino et al. ................. | 433/173 |
| 4,713,006 A | * | 12/1987 | Hakamatsuka et al. . | 433/173 X |
| 5,002,488 A | * | 3/1991 | Homsy ..................... | 433/173 X |
| 5,123,844 A | * | 6/1992 | Wakai et al. ............ | 433/173 X |
| 5,427,526 A | * | 6/1995 | Fernandes ................ | 433/175 X |

* cited by examiner

Primary Examiner—Nicholas D. Lucchesi
(74) Attorney, Agent, or Firm—Volpe and Koenig, P.C.

(57) ABSTRACT

Plugs for use in sinus lift and augmentation techniques have a mushroom-like shape and having of a substantially cone-shaped body with an integral head of enlarged diameter. The plugs are preferably formed of donor cadaver bone, osteosite or hatogens. The plugs, in one embodiment, are formed of universal sizes and are preferably "CAD CAM" cut, based on a scan of the orifice. The plugs have a fluted or corrugated-like periphery and are preferably swaged into a previously prepared cavity, the fluted configuration preventing rotation of the plug. An implant is then counter-sunk into the core plug. The core plugs, once in place, promote bone growth and integration as self to enhance and provide a bed of rich bone in compromised and deficient areas structurally and esthetically. A set of tapped drills range from 2.8 mm up to 7.5 mm in diameter and lengths of 8 mm–15 mm can be used and standard plugs can be used in place of CAD CAM (i.e., "custom") cutting.

28 Claims, 2 Drawing Sheets

US 6,343,931 B1

BONE AUGMENTATION METHOD AND APPARATUS

FIELD OF THE INVENTION

The present invention relates to bone augmentation apparatus and techniques and more particularly to apparatus and method for bone augmentation utilized anywhere in the body. In one example, in dentistry, the technique is comprised of inserting an anti-rotational core plug which is swaged into place, whereupon an implant is counter-sunk into the core plug which is formed of a material that promotes bone growth such as 1) autogenesis. 2) cadaver (synthetic) and a combination thereof.

BACKGROUND OF THE INVENTION

There are a number of situations requiring implantation of a prosthesis. As one particular example, when it becomes necessary to remove a diseased tooth, it is typically replaced with a prosthesis. Conventional techniques do not utilize an autogenesis, cadaver, and synthetic member employed in the manner of the present invention.

BRIEF DESCRIPTION OF THE INVENTION

The present invention is characterized by comprising method and apparatus for eliminating such inordinate delays, deficiency and failure to obtain an optimum cavity shape and further providing a technique in which bone growth is promoted and one in which the conventional procedure is greatly simplified and which is more predictable in shape and density. The present invention is characterized by comprising a technique which utilizes a core plug having a mushroom-like shape with a tapered body portion having an integral head portion of larger diameter. The core plug is formed of a suitable material, such as cadaver bone, a mixture of synthetic bone with osteogen or hatogens. The core plugs are formed in a plurality of sizes or are "CAD CAM" cut (i.e., "custom cut") according to the scan of an orifice from which the diseased tooth has been removed or to fit a pre-existing cavity.

The bone core plugs are swaged into place and preferably have a fluted, or grooved, convex periphery to prevent rotation of the core plug and to assure a firm force-fit within the cavity. A prosthesis can be counter-sunk into the core plug. The core plug promotes bone growth, and integrates into the bone, thus providing an excellent site for replacement prosthesis, which is far superior to any conventional device or method.

The current deficiencies encompass both function and esthetic. The present invention provides a stable platform for predictable achievement of support for implants.

OBJECTS OF THE INVENTION

It is therefore one object of the present invention to provide a novel method and apparatus for providing bone implants utilizing novel core plugs to add girth to bone in severe atropical bone areas.

Another object of the present invention is to provide bone implants using novel core plugs.

Still another object of the present invention is to provide bone implants utilizing novel core plugs which promote bone growth.

Still another object of the present invention is to provide method and apparatus for providing implants utilizing a technique which completes the entire implant operation on site within a dental office and requiring only one visit.

BRIEF DESCRIPTION OF THE FIGURES

The above objects will become apparent when reading the accompanying description and drawings in which.

DETAILED DESCRIPTION OF THE INVENTION AND PREFERRED EMBODIMENTS THEREOF

Figure 3:
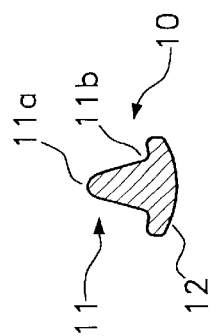
FIG. 3 shows a typical core plug employed in the method of the present invention.
Figure 3A:
FIGS. 3a and 3b show sectional views of the core plug of FIG. 3.
Figure 3B:

FIG. 3 shows a core plug 10 designed in accordance with the principles of the present invention and comprised of a main body portion 11 and an integral, enlarged head portion 12. The main body portion 11 preferably, is slightly tapered and is provided with a rounded tip 11a. However, the body portion may be of a constant diameter and/or have outwardly bulging portions, if desired, for some applications. The larger diameter end 11b is integrally formed with the head portion 12. The external surface of the core plug 10 is preferably fluted, as shown in FIG. 3a or is provided with a plurality of grooves 11c extending along the length of the main body portion 11, as shown in FIG. 3b. FIG. 3 shows a core plug with a substantial hemispheric shaped head 12. The core plug is preferably formed of a material, such as freeze-dried cadaver bone, autogenous material, as well as a mixture of a synthetic bone with an osteogen hormone or any other suitable hormone capable of stimulating growth.

Figure 1:
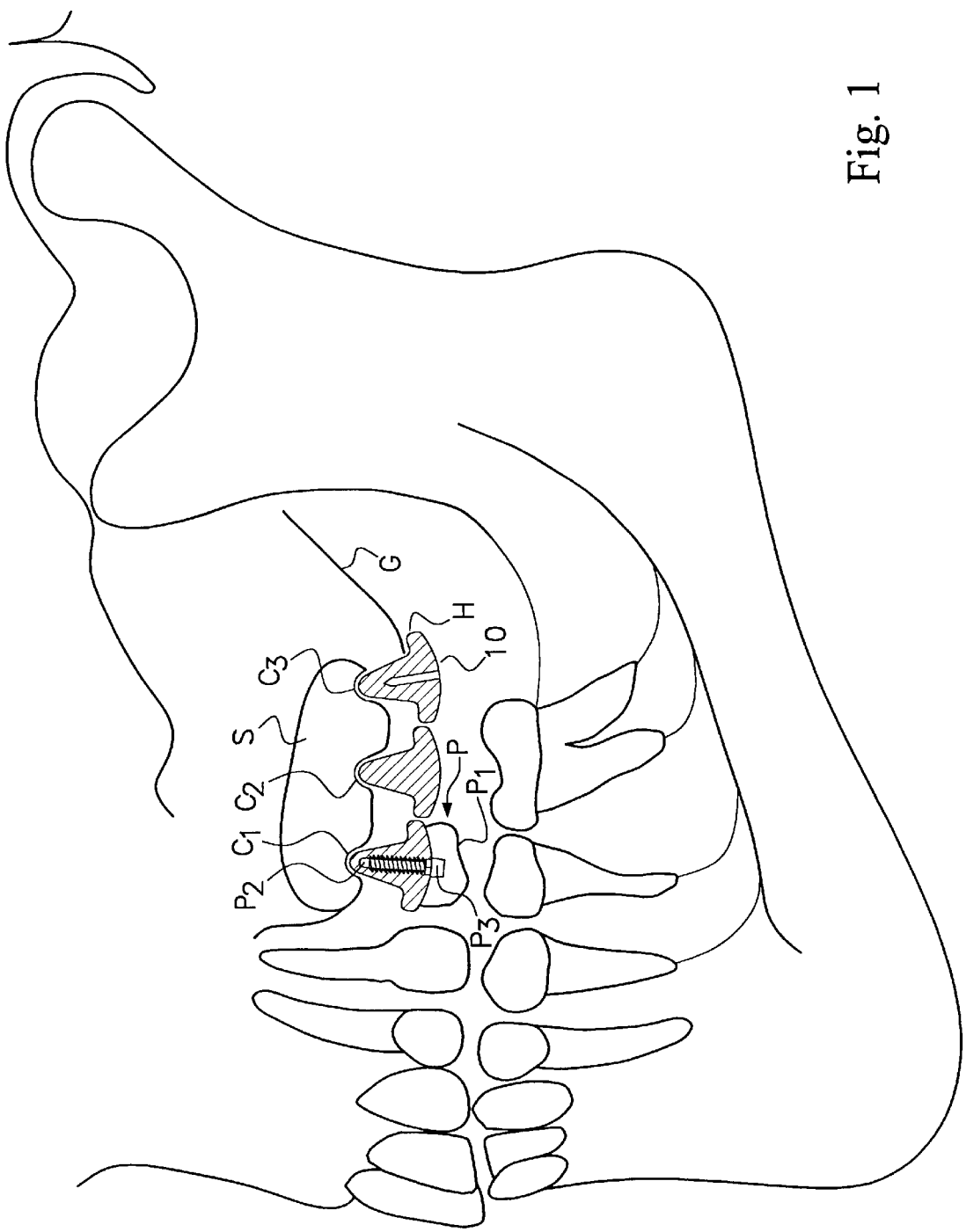
FIGS. 1 and 2 show side views of a upper portion of the human head with the teeth and bone structure exposed to facilitate a better understanding of the invention.

FIG. 1 shows a partial view of a patient's teeth in which teeth have been removed due to disease or other state, which extractions have lead to the cavities C1, C2, and C3.

The extraction site is preferably scanned to accurately determine its size and configuration, typically by equipment such as, for example, the SEREC 1.11 and SEREC 2, manufactured by Sirona Dental Systems of Bensheim, Germany, or any other device having similar capabilities. Using the data obtained through the scanning operation, a core plug, such as the core plug 10, shown in FIG. 3, is CAD CAM cut to appropriate size, which operation is completed in the dental office, therefore avoiding the necessity of multiple visits in order to complete the procedure, and reduce wait-time. Also standard cores with pre-drilled holes H (see FIG. 2) which are compatible sizes of approximately 4/5/6/8 mm., respectively, and being slightly smaller than bone size may be utilized.

The core plug is preferably swaged into position by tapping the core plug into position with a suitable swaging tool (not shown for purposes of simplicity). However, any other suitable technique may be employed. The fluted configuration of FIG. 3a (or grooves of FIG. 3b) in the main body portion permit compression of the core plug, as well as providing excellent gripping forces which prevent rotation of the core plug, once swaged into position. FIG. 1 shows two such core plugs swaged into position and extending through the bone B and into sinus S to increase sinus lift. The dome shaped portion of the core plug 10 is greater in size than the opening H and overlies the portion G of bone (see FIG. 1).

Figure 2:
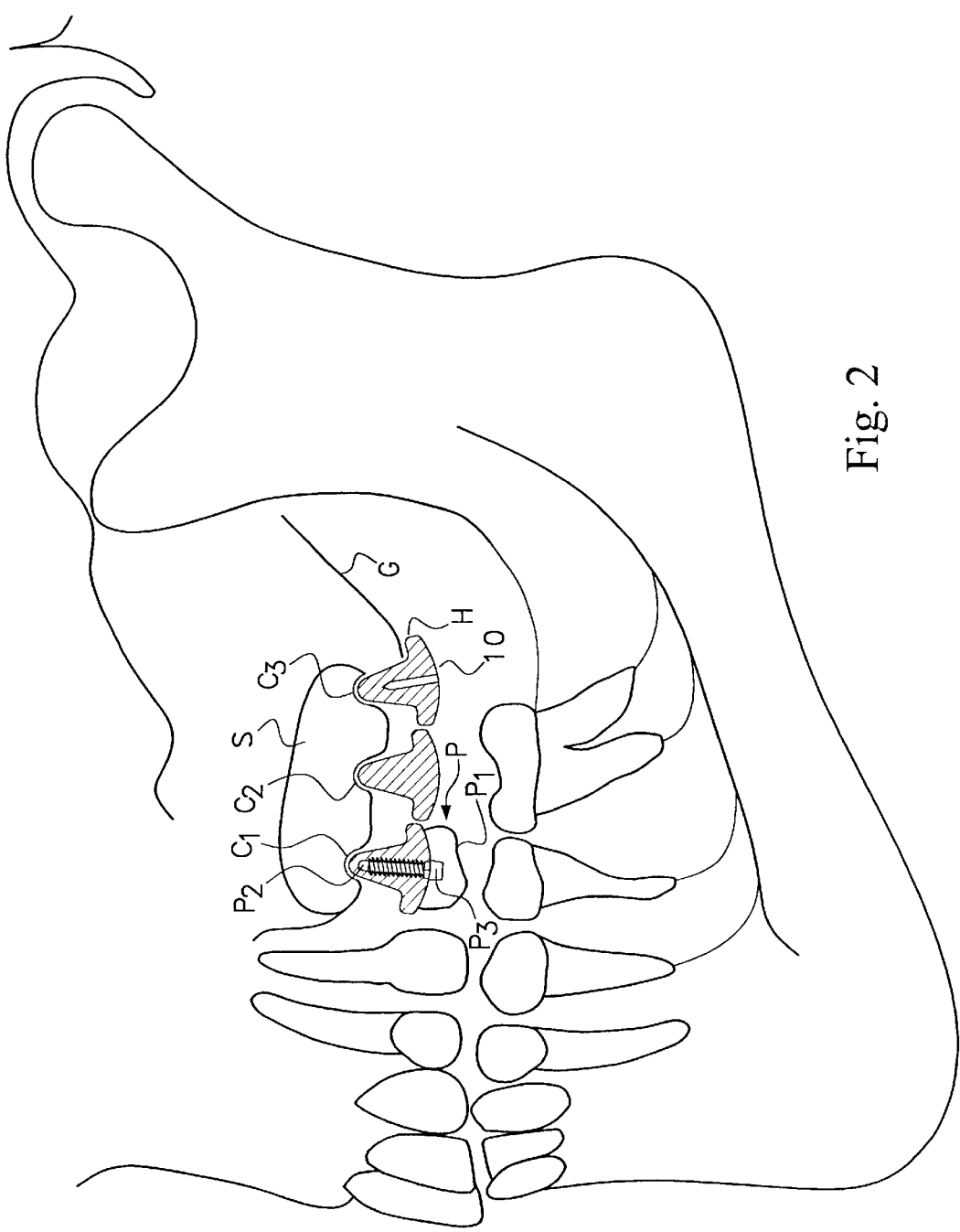

The prosthesis P, as shown in FIG. 2, which is comprised of a tooth portion P1 having a suitable enamel surface which color-coordinates with the other teeth, having an anchoring portion P2 which may be a tapered threaded portion for threadedly engaging the core plug, as well as a securement portion P3, which secures the anchoring portion.

Where necessary, a hole of an appropriate diameter may be drilled into the core plug as a "starting means" for insertion of the anchoring portion P2. Means may be utilized to accurately locate the starter opening such as pre-drilled cores or pre-implanted plugs.

In some applications, it may be desired or even necessary to reshape the cavity from which the diseased tooth has been extracted in order to provide a cavity of more uniform shape. This may be accomplished by any conventional technique or alternatively, may be accomplished through the use of the tool described in co-pending application U.S. patent application Ser. No. 09,388,402, filed Sep. 1, 1999, (REG-PT001) [(REG 3.0-001)] now Issued U.S. Pat. No. 6, 300,324 B1 by the inventor of the present application.

The core plug 10 promotes bone growth providing a bond between the core plug and the cavity, which is far superior to that capable of being obtained through conventional techniques. The method and apparatus of the present invention further reduces the time for performing the procedure as well as eliminating the need for multiple visits, typically, resulting from the need to obtain a properly sized shape and esthetics. This will allow greater volume of bone sinus lifting and bone girth in one visit with little or no resorption.

The core plugs 10 are preferably stocked in a variety of sizes over a given range. For example, for dental applications, the range may extend from a lower end average diameter of the main body portion of 3–6 mm to an upper end of an average diameter of 5–8 mm. The core plugs may also be of different lengths, such as a range of from 8 to 15 mm. Stocking a plurality of core plugs reduces the time required for the cutting phase of the core plug and further simplifies the cutting phase. The core plugs may also be stocked in tapers in a range of 10–25 degrees.

Although the embodiment described herein recites implantation for dental prostheses, it should be understood that the present invention may be utilized in other applications, such as, other oral, as well as non-oral implants, such as orthopedic prostheses or surgical procedures requiring precise dimensional modifications, for example. Of course, the size ranges stocked for use in applications other than dental, would be necessarily larger and a function of the specific application.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention described herein.

What is claimed is:

1. A method for implanting a prosthesis comprising:
    (a) forming a core plug which is formed of a material which promotes and stimulates bone growth said material being selected from a group comprising an autogenis material, freeze-dried cadaver, a hybrid of synthetic bone and osteogen and a material containing a hormone stimulating growth hormone;
    (b) inserting the core plug into a cavity from which a bone portion has been removed, so that the insertion causes the core plug to be intimately secured within said cavity; and
    (c) inserting a prosthesis into said core plug.

2. The method of claim 1 wherein step (b) is performed by swaging the core plug into the cavity.

3. The method of claim 2 wherein step (a) further comprises providing an outer peripheral portion of the core plug which is to be inserted into the cavity with a plurality of grooves therearound to facilitate insertion during swaging and further to prevent rotation of the core plug once swaged into place.

4. The method of claim 2 wherein step (a) further comprises providing an outer peripheral portion of the core plug which is to be inserted into the cavity with a fluted peripheral surface portion to facilitate insertion during swaging and further to prevent rotation of the core plug once swaged into place.

5. The method of claim 1 further comprising:
    initially forming a small diameter hole in said core plug preparatory to insertion of the prosthesis.

6. The method of claim 1 wherein the core plug is provided with a pilot hole for receiving an anchor.

7. The method of claim 1 wherein a fixture implant is placed in the core plug prior to insertion of the core plug into the cavity.

8. The method of claim 1 wherein step (a) further comprises forming the core plug of a mushroom-like shape.

9. The method of claim 1 wherein step (a) further comprises forming the core plug of dowel pin shape with serrated or fluted sides.

10. The method of claim 1 wherein step (a) further comprises forming the core plug of a mushroom-like shape which is comprised of a tapered main body portion and an integral dome-shaped bead portion.

11. The method of claim 10 wherein step (b) further comprises urging the core plug into said cavity so that the dome-shaped end extends beyond an open end of the said cavity.

12. The method of claim 1 wherein step (c) further comprises providing a prosthesis with a threaded portion for threaded insertion into the core plug.

13. The method of claim 1 further comprising the step of scanning said cavity to determine its size and shape; and
    cutting said core plug to the appropriate size and shape according to the result s of the scan.

14. A core plug for use in bone implantations and the like, said core plug having a mushroom-like shape comprised of an annular-shaped main body portion and an integrally formed, dome-shaped head portion, said core plug being formed of a material which promotes and stimulates bone growth said material being selected from a group comprising an autogenis material, freeze-dried cadaver, a hybrid of synthetic bone and osteogen and a material containing a hormone stimulating growth hormone.

15. The core plug of claim 14 wherein said main body portion has a tapered-shape.

16. The core plug of claim 14 wherein the free end of the core plug main body portion has a rounded end.

17. The core plug of claim 14, wherein the periphery of said main body portion is provided with a plurality of grooves to facilitate and enhance gripping of the main body portion with the engaging surfaces of the cavity into which the core plug is inserted.

18. The core plug of claim 14, wherein the periphery of said main body portion is provided having a fluted periphery.

19. The core plug of claim 14 wherein the core plug is formed of a material which is compatible with the cavity into which it is inserted to prevent a negative reaction to the core plug.

20. The core plug of claim 14 wherein at least the main body portion is formed of a material which promotes bone growth.

21. The method of claim 1 wherein step (a) further comprises urging the core plug into said cavity to cause sinus lift.

22. The method of claim 1 wherein step (b) further comprises urging the core plug into said cavity to increase a volume of the cavity.

23. The method of claim 1 wherein step (b) further comprises reshaping the cavity with a drill prior to insertion of the core plug.

24. The method of claim 1 wherein step (b) further comprises reshaping the cavity with a drill including selecting a drill size smaller than a size of said core plug and swaging said core plug into said cavity.

25. A method of augmenting bone in a deficient or esthetically compromised or function compromised area, comprising:
   (a) forming a core plug, which is made of a material which promotes and stimulates bone growth said material being selected from a group comprising an autogenis material, freeze-dried cadaver, a hybrid of synthetic bone and osteogen and a material containing a hormone stimulating growth hormone;
   (b) inserting the core plug into a cavity from which a bone portion has been removed, so that the insertion causes the core plug to be in intimate engagement with walls of the cavity.

26. A method for implanting a prosthesis, comprising:
   (a) providing a kit containing a plurality of core plugs varying in diameter over a range of 3 to 8 mm and length over a range of 8–15 mm said material being selected from a group comprising an autogenis material, freeze-dried cadaver, a hybrid of synthetic bone and osteogen and a material containing a hormone stimulating growth hormone;
   (b) selecting one of said core plugs;
   (c) inserting the selected core plug into said cavity from which a bone portion has been removed; and
   (d) swaging the selected core plug into said cavity to increase a volume of said cavity.

27. The method of claim 26 wherein step (c) further comprises the steps of:
   reshaping said cavity with a drill prior to insertion of said selected core plug.

28. The method claim 27 wherein step (c) further comprises selecting a drill of size smaller than the selected core plug.

* * * * *